US010629309B2

(12) United States Patent
Van Lierde et al.

(10) Patent No.: US 10,629,309 B2
(45) Date of Patent: Apr. 21, 2020

(54) METHOD AND SYSTEM FOR 3D ROOT CANAL TREATMENT PLANNING

(71) Applicants: MAILLEFER INSTRUMENTS HOLDING SÀRL, Ballaigues (CH); DENTSPLY IMPLANTS NV, Hasselt (BE)

(72) Inventors: Carl Van Lierde, Meerbeke (BE); Veerle Pattijn, Kessel-Lo (BE); Paul-Henri Vallotton, Pampigny (CH)

(73) Assignees: MAILLEFER INSTRUMENTS HOLDING SARL, Ballaigues (CH); DENTSPLY IMPLANTS NV, Hasselt (BE)

( * ) Notice: Subject to any disclaimer, the term of this patent is extended or adjusted under 35 U.S.C. 154(b) by 407 days.

(21) Appl. No.: 15/712,162

(22) Filed: Sep. 22, 2017

(65) Prior Publication Data
US 2018/0075210 A1    Mar. 15, 2018

Related U.S. Application Data

(63) Continuation of application No. 14/342,694, filed as application No. PCT/EP2012/066577 on Aug. 27, 2012, now Pat. No. 9,805,167.

(30) Foreign Application Priority Data

Sep. 5, 2011 (GB) .................................. 1115265.9

(51) Int. Cl.
*G06F 17/50* (2006.01)
*G16H 50/50* (2018.01)
(Continued)

(52) U.S. Cl.
CPC .............. *G16H 50/50* (2018.01); *A61C 5/40* (2017.02); *G06T 19/20* (2013.01); *A61C 13/0004* (2013.01); *G06T 2210/41* (2013.01)

(58) Field of Classification Search
CPC ...... G16H 50/50; A61C 5/40; A61C 13/0004; G06T 19/20; G06T 2210/41; G09B 9/00
(Continued)

(56) References Cited

U.S. PATENT DOCUMENTS 6,152,731 A * 11/2000 Jordan ............... A61C 13/0003
433/69
6,905,337 B1 6/2005 Sachdeva
(Continued)

FOREIGN PATENT DOCUMENTS

CN    1471061    1/2004
CN    101797188    8/2010
(Continued)

OTHER PUBLICATIONS

"The History of Root Canal treatment" from the website "https://gentlewave.com/resources/the-history-of-root-canal-treatment" retrieved on Apr. 13, 2017; 3 pages.
(Continued)

*Primary Examiner* — Dwin M Craig
(74) *Attorney, Agent, or Firm* — Young & Thompson

(57) ABSTRACT

A three-dimensional computer model of the patient's tooth, including the pulp chamber and root canals, is created by combining at least one grey value image of the tooth and/or surface information about at least part of the intra-orally visible part of the tooth with a statistical, parameterized shape model of each tooth type (upper or lower incisors, canines, pre-molars, molars) as the patient's tooth to be treated. This allows for planning and/or simulation of one or more root canal treatments on the computer model of the patient's tooth and that the dentist or dental specialist is given qualitative and/or quantitative information by the system in order to aid in adequately analyzing the risks
(Continued)

related to performing the root canal treatment with the proposed or user-selected endodontic tools.

20 Claims, 3 Drawing Sheets

(51) Int. Cl.
*A61C 5/40* (2017.01)
*G06T 19/20* (2011.01)
*A61C 13/00* (2006.01)

(58) Field of Classification Search
USPC .............................................................. 703/1
See application file for complete search history.

(56) References Cited

U.S. PATENT DOCUMENTS

| | | | |
|---|---|---|---|
| 2004/0185422 A1 | 9/2004 | Orth et al. | |
| 2005/0214716 A1 | 9/2005 | Weber et al. | |
| 2006/0063135 A1 | 3/2006 | Mehl | |
| 2007/0238065 A1 | 10/2007 | Sherwood et al. | |
| 2009/0148809 A1 | 6/2009 | Kuo et al. | |
| 2009/0187393 A1 | 7/2009 | Van Lierde et al. | |
| 2009/0298017 A1* | 12/2009 | Boerjes | A61B 5/4547 433/214 |
| 2010/0145898 A1 | 6/2010 | Malfliet et al. | |
| 2011/0059413 A1 | 3/2011 | Schutyser et al. | |

FOREIGN PATENT DOCUMENTS

| | | |
|---|---|---|
| EP | 0 904 743 | 3/1999 |
| EP | 1459702 | 9/2004 |
| GB | 1108002 A | 3/1968 |
| GB | 2440267 | 1/2008 |
| GB | 1108002.5 | 5/2011 |
| JP | 0919443 | 1/1997 |
| JP | 2004305610 | 11/2004 |
| JP | 2006-502817 A | 1/2006 |
| JP | 2007-525289 A | 9/2007 |
| JP | 2009-537190 A | 10/2009 |
| JP | 2010524529 | 7/2010 |
| KR | 10-2005-0059134 A | 6/2005 |
| RU | 2400178 C1 | 9/2010 |
| WO | 2005/086058 A1 | 9/2005 |
| WO | 2010028025 | 3/2010 |
| WO | WO 2010/097089 | 9/2010 |
| WO | 2011101447 | 8/2011 |
| WO | 2012155998 | 11/2012 |

OTHER PUBLICATIONS

Great Britain Search Report issued in Application No. GB1115265.9 dated Dec. 21, 2011.
Fleute et al., "Nonrigid 3-D/2-D Registration of Images Using Statistical Models", LNCS 1679, 1999, pp. 138-147.
Gao et al., "An Application Framework of Three-dimensional Reconstruction and Measurement for Endodontic Research", JOE, 2009, vol. 35, No. 2, pp. 269-274.
Gollmer et al., "Evaluation and Enhancement of a Procedure for Generating a 3D Bone Model Using Radiographs", Advances in Medical Engineering, Proceedings in Physics, 2007, vol. 114, pp. 163-168.
Gollmer et al., "Registration Algorithm for Statistical Bone Shape Reconstruction from Radiographs—An Accuracy Study", Proceedings of the 29th Annual International Conference of the IEEE EMBS, 2007, pp. 6375-6378.
Lyroudia et al., "Virtual Endodontics: Three-Dimensional Tooth Volume Representations and their Pulp Cavity Access", Journal of Endodontics, 2002, vol. 28, No. 8, pp. 599-602, XP005355034.
Blanz et al., "Biogeneric tooth: a new mathematical representation for tooth morphology in lower first molars", European Journal of Oral Sciences, 2005, vol. 113, vol. 333-340.
Patel, S., "New dimensions in endodontic imaging: Part2. Cone beam computed tomography", International Endodontic Journal, 2009, vol. 42, pp. 463-475.
Tang et al., "2D/3E Deformable Registration Using a Hybrid Atlas", LNCS 3750, 2005, pp. 223-230.
International Search Report, dated Jan. 9, 2013, from corresponding PCT application.
Chinese Search Report dated May 17, 2016; Application No. 201280043042.2.
Japanese Office Action dated Jun. 1, 2016, with English Translation; Application No. 2014-527610.
Japanese Office Action issued in Application No. 2016-171150, dated Sep. 4, 2017.
Korean Office Action issued in Application No. 10-2014-7006092, dated Aug. 21, 2018, with English Abstract.
European Office Action EP 12756415.1, dated Dec. 20, 2017.
Russian Office Action dated Oct. 24, 2019, in corresponding Russian Application No. 2016134616/14, with English translation.

* cited by examiner

METHOD AND SYSTEM FOR 3D ROOT CANAL TREATMENT PLANNING

The present invention relates to a method and system for 3D root canal treatment planning as well as software for carrying out such methods.

BACKGROUND

Root canal treatment is a tooth-saving treatment that eliminates infections, protects the decontaminated tooth from future infections, and—if needed—restores the tooth at crown level either with or without use of a post. During this treatment the root canals, which mainly contain the nerve tissue and blood vessels are cleaned, shaped, decontaminated and subsequently filled with an inert filling such as gutta percha. In cases where the remaining tooth structure is insufficient to support a proper reconstruction of the dental crown, a metal or glass fiber post is positioned in one of the root canals and a core build-up is created in order to support and provide retention for the prosthetic restoration (i.e. crown).

Root canal treatment can fail or lead to complications due to several reasons, e.g. insufficient cleaning of the root canals, incomplete filling of the root canals, untreated canals since these were missed by the practitioner, root perforations or file fracture during shaping of the canals, root fractures . . . .

According to literature the use of 3D tooth assessment can reduce the risk of complications during root canal treatment. Cone beam computed tomography (CBCT) for instance can be used in the management of endodontic problems, i.e. in the assessment of the true size, extent, nature and position of peri-apical and resorptive lesions, in the assessment of root canal anatomy, root fractures, and the nature of the alveolar bone topography around teeth, or in the planning of endodontic surgery (cf. *New dimensions in endodontic imaging: Part 2. Cone beam computed tomography. International Endodontic Journal*, 42, 463-75, 2009). Cone beam computed tomography provides more comprehensive diagnostic data compared to intra-oral radiography, hence resulting in more accurate diagnosis and monitoring, and therefore improving the management of endodontic problems.

Micro-computed tomography (µCT) has been used in academic settings, on extracted teeth for three-dimensional reconstruction and assessment of tooth and root canal morphology for endodontic research purposes (cf. *An application framework of three-dimensional reconstruction and measurement for endodontic research*, Yuan Gao, Ove A. Peters, Hongkun Wu, Xuedong Zhou, *J Endod* 2009; 35:269-274). The internal and external anatomies of the tooth were reconstructed and the dimensions of root canal and radicular dentin quantified. The root canal dimensions were calculated by first defining the root canal middle line and then calculating the distance from the middle line to the root canal surface. These distances were subsequently visualized by means of a colour-code on the root canal surface. The minimal distance from the external root surface to the root canal surface was also calculated and visualized by means of a colour-code. Then the evaluation of the root canal preparation was performed by registering pre- and post-preparation images of the tooth. In both image sets the root canal was segmented and visualized in 3D for a graphic comparison of the change of canal shape, namely the amount of dentin removal during canal preparation. In addition the perforation risk during removal of a broken instrument could be analysed. After virtually simulating the removal of the said broken instrument by means of a user specified trepan/trephine on the computer, a thickness analysis on the remaining root was performed, as a means to quantify the risk of root perforation.

UK patent application, 1108002, Method and system for establishing the shape of the occlusal access cavity in endodontic treatment, describes the use of a three-dimensional computer model of the tooth including the pulp chamber and the root canals in order to define the optimal shape and geometry of the occlusal access cavity to the tooth roots prior to root canal treatment.

While the use of 3D computer images and models has been reported for the preparation of root canal treatment, the available prior art fails to provide a method that is usable in the daily clinical practice. Current CBCT technology does not provide the required image resolution to allow for planning of the root canal treatment, since the root canals are often hardly if at all distinguishable from noise in the images. Even in cases where the root canals can be discerned, the reliability of measurements performed on the images, e.g. with respect to the canal dimensions, is insufficient to provide added value when planning the clinical intervention. In addition, radiation doses required for CBCT imaging can drastically exceed those of traditional X-rays, potentially adding risk to the patient, and making the technique currently unsuited for most endodontic indications. µCT imaging is even less suitable: currently, there is no commercially available equipment for acquiring µCT images on patients, since fields of view are too limited, required radiation doses too high and data acquisition times too long with this technology. µCT imaging currently only works on extracted teeth, in specific set-ups for research purposes.

SUMMARY OF THE INVENTION

An object of the present invention is to provide a method and system for 3D root canal treatment planning. Embodiments of the present invention aim to overcome one or more of the problems described above and to provide a method and system that aids the dentist or dental specialist in more accurately planning primary root canal treatment and/or root canal retreatment. An aspect of the present invention is the use of simulation to provide a qualitative and/or quantitative assessment of treatment related risks.

A significant advantage of embodiments of the current invention is that case or patient specific planning can be performed in 3D without the need for 3D imaging techniques exposing patient to radiation doses higher than conventional X-ray, while still providing detailed information about the anatomical characteristics of the teeth.

Another aspect of the current invention is that a three-dimensional computer model of the patient's tooth, including the pulp chamber and root canals, is created by combining at least one 2D grey value image of said tooth and/or surface information about at least part of the intra-orally visible part of the tooth with a statistical, parameterized shape model of each tooth type (upper or lower incisors, canines, pre-molars, molars) as the patient's tooth to be treated.

Yet another aspect of the current invention is that the method and system allows for planning and/or simulation of one or more root canal treatments on the 3D computer model of the patient's tooth and that the dentist or dental specialist is given qualitative and/or quantitative information by the system in order to aid in adequately analysing the risks related to performing the root canal treatment with the proposed or user-selected endodontic tools.

It is therefore a significant advantage of the current invention that it aids the dentist or dental specialist in selecting the optimal tools for performing a root canal treatment prior to the treatment itself.

These and further objects, features and advantages of the invention will become apparent from the following detailed description wherein reference is made to the figures in the accompanying drawings.

DESCRIPTION OF PREFERRED EMBODIMENTS

The present invention will be described with respect to particular embodiments and with reference to certain drawings but the invention is not limited thereto but only by the claims.

According to a preferred embodiment of the invention a first step according to a method for simulating root canal treatment simulation consists in creating and visualizing a three-dimensional model of a patient's tooth including the pulp chamber and the root canals. Therefore, the system consists at least of a computer including computer programs which can be utilized with the method for visualizing said three-dimensional model.

Figure 3:
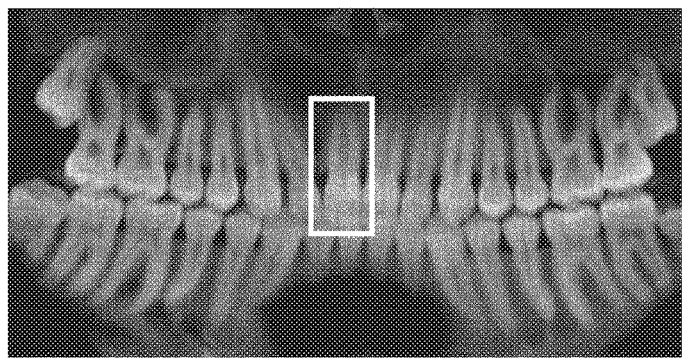
FIG. 3 shows an example of 2D grey value image of patient's tooth.
Figure 4:
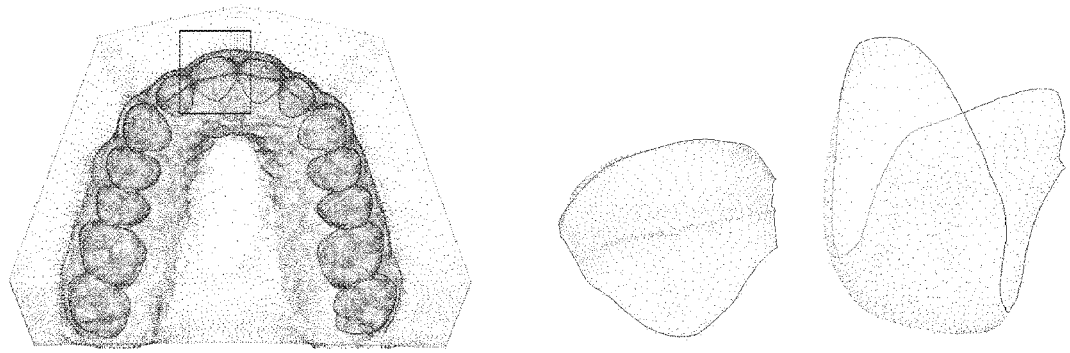
FIG. 4 shows an example of 3D surface information of intra-orally visible part of patient's tooth, obtained by optically scanning the plaster model of the patient's dentition.
Figure 5:
FIG. 5 shows an example of 3D model of patient's tooth including pulp chamber and root canals.

With reference to FIGS. 3 to 5, according to one embodiment the 3D model of the tooth with pulp chamber and root canals is generated based on the combination of 3D imaging data of the crown and one or more 2D radiographs of the tooth. Therefore the 3D crown information of the respective tooth is digitized. This can be done using different methods. A first method uses a conventional impression of the patient's teeth. This negative impression is used for making a positive impression, e.g. by pouring a model using plaster or other suitable material, whose 3D surface is then captured and digitised, e.g. scanned either optically or by CT techniques (e.g. µCT scanner, CBCT scanner . . . ). Alternatively, the negative impression itself is used to obtain the 3D surface details, e.g. the impression is scanned. In a second method the crown of the tooth is digitized by taking an intra-oral scan of the respective tooth. In a third method 3D imaging data collected during a volumetric scan such as with a CBCT scanner exam is used.

The digital crown information is combined with the 2D radiographs by means of an expert system in order to construct a 3D model of the tooth including the pulp chamber and the root canals. The expert system preferably includes a statistical shape model in order to calculate the 3D model of the tooth as accurately as reasonably possible based on the 2D radiograph data combined with the 3D crown data. The statistical shape model is preferably generated for each type of tooth separately. It can comprise at least a parameterized 3D (volumetric or surface) representation of the tooth, potentially extended with associated parameterized 2D radiographs. Variances in the 3D representation are linked to associated variances in the 2D radiographs. Examples of such variances are tooth morphology, variation in number of cuspids, variation in size and shape of the pulp chamber, number of roots and root canals, variation in size and shape of root canals . . . . The technique used to combine one or multiple 2D images with a statistical shape model in order to calculate a patient specific 3D model may for instance consist in calculating the projection outlines (e.g. 2D curves) of the statistical shape model in planes estimated to correspond to the projection planes of the 2D images. In the 2D images, the edges of the tooth are calculated (e.g. by means of edge detection algorithms). The 3D statistical shape model is next modified (using previously mentioned parameter values) and repositioned relative to the coordinate system defined by the 2D images, all the while reassessing the outlines, until the outlines of the 3D model match (according to a predefined criterion) the edges calculated on the 2D images. The resulting modified 3D statistical shape model is then used as 3D model for the specific case.

Alternatively, if the covariances between the statistical shape model and its corresponding parameterized 2D radiographs are known, it may be sufficient to modify the 2D radiographs associated with the statistical shape model by varying the parameter values dictating its variances, to match the 2D radiographs obtained in the mouth of the patient, in order to directly obtain the desired corresponding 3D model of the tooth (i.e. external geometry, shape and location of the pulp chamber and tooth roots).

The above-described methods can be applied for generating accurate 3D models of individual teeth either for primary root canal treatment or retreatment.

Once the tooth and root canals are visualized in 3D, the next steps according to a method for 3D root canal treatment planning can start; i.e. planning and/or simulation of the root canal treatment and calculating feedback to aid in the determination of the optimal way to go about the treatment. These next steps can be performed in any arbitrary order and are not limited by the following examples.

According to a first illustrative example, the system allows for planning the root canal treatment by determining an optimal file sequence (i.e. diameter of files and their working length) for reaming a root canal. Therefore the system allows for defining the midlines of the root canals either manually or (semi-)automatically. In a manual approach the user has to scroll through parallel 2D sectional images (axial, bucco-lingual or mesio-distal) and draw a line sequence or a curve (e.g. polynomial or spline) by manually indicating succeeding centre points of the root canal within the 2D sectional images. In a semi-automatic approach the user starts with selecting a root canal by for instance indicating apical and occlusal end of the root canal, or by marking the surface of the root canal, or by any other method. Subsequently, an algorithm defines a number of equidistant parallel sections (e.g. axial, or bucco-lingual, or mesio-distal) in which the contour of the root canal (i.e. the intersection curve of the root canal surface and the 2D plane defining the section) is calculated as well as the centre point of this contour. The centre point can be calculated in different ways; e.g. as the centre of gravity of the surface delineated by the contour of the root canal, or as the centre of the largest inscribed circle of the root canal contour, or as the centre of the smallest circumscribed circle of the root canal contour, or as the centre of the best fitting ellipse/circle of the root canal contour, or by yet another method. Calculating a curve through these centre points, results in a midline for the root canal. According to another approach the midline can be improved by determining the contours and their centre points of the root canal in multiple orthogonal sections and determining the best fitting curve through all the resulting centre points. According to yet another approach the midline determined based on one of the above described approaches (i.e. by means of parallel equidistant 2D sections) can be iteratively improved by defining sections perpendicular to this midline at equal distances along this midline, determining the contour of the root canal and its centre point in these new 2D sections, and defining a new curve through these new centre points. This method can be repeated several times in order to obtain an accurate description of the midline of the root canal.

Based on the midline for each root canal new sectional images perpendicular to this midline and at equal distances along this midline can be generated and visualized. Within these 2D sections the minimal circle circumscribing the contour of the root canal can be calculated automatically and its diameter—optionally increased with a predefined constant value—used to determine the minimal diameter of the file needed for reaming the root canal in that section. Based on this succession of diameter values along the root canal a sequence of best fitting files for reaming each individual root canal is determined. A first method is by outlining the minimal diameter values for the file for the succeeding sections along a straight line at the distances of the respective sections and calculating the smallest cone that circumscribes these diameter values. A set of files, available through a library, is fitted in this cone at maximum depth (i.e. until the file makes contact with the cone). Then the difference between this cone volume and the total volume by combining all files is calculated in order to quantify the reaming of the root canal by using this sequence of files. In order to improve the reaming of the root canal the files can be positioned deeper than at maximum depth. The increase in depth position for each file can either be a fixed predefined distance or be calculated to completely cover the circumscribed cone volume but with a minimal additional volume removal, or be calculated to completely cover the circumscribed cone volume but with a predefined limited sequence of files. The result is a sequence of files with the corresponding depth to which each file must be used (working length). According to a second method a file is modelled using its 3D CAD/CAM information and fitted—simulating necessary bending of the file corresponding with the 3D curvature of the root canal—into the root canal to maximal depth, which will depend on the size of the file and the size of the root canal. This fitting action is repeated for files with increasing diameter, and as such a sequence of files and their working length is determined for reaming the root canal. Similar to the first method the maximal depth of a file can also be increased with either a predefined fixed value or be calculated in order to either optimize the reaming of the root canal or limit the number of files necessary for reaming the root canal. In this 3D approach the optimization of the root canal reaming is done by comparing the volume reamed by the file sequence with the real root canal volume. The reaming is optimal if the root canal volume is completely reamed with a minimal reaming of additional root material. According to a preferential implementation, material properties of the endodontic instruments (e.g. files) are used during the simulation of the bending to calculate and visualize (e.g. by means of a color code—green=low; orange=moderate; red=high) the risk of instrument fracture.

According to a preferred step of the current invention the system allows for quantitative and/or qualitative feedback in order to aid in adequately analyzing the risks related to performing the root canal treatment.

As a first example the system can allow for visualizing the wall thickness of the root along the root canal to provide feedback regarding for instance the risk of root fracture or root perforations during root canal treatment. Therefore the distance between the surface of the root canal and the external surface of the tooth/tooth root is calculated. Given that a triangulated surface representation may be used to visualize the different anatomical structures (crown, tooth root; root canal, pulp chamber, etc.) the distance can be determined in different ways. A first method is by calculating the distance between each node of triangles on the outer root surface and the closest point on the root canal surface. A second method is by calculating the distance between each node on the root canal surface and the closest point on the outer root surface. A third method is by calculating the distance from each node on the root surface along its normal to the root canal surface. Any other method for distance calculation can be used. These numerical values can be visualized for instance by means of a colour code on the 3D model or in the 2D sections in order to provide the user the necessary graphical feedback regarding the thickness of the root along the root canal. Other methods for visualizing numerical values are isometric lines either on the 3D surface or in the 2D sections, or labelling.

Another valuable parameter is the distance from each point of the root canal surface to the outer root surface but calculated along the corresponding radial direction within the plane perpendicular to the midline of the root canal. This value, or this value reduced with a safety value specifying the minimally desired remaining root wall thickness, gives the user feedback regarding the maximally allowable increase of the file diameter for the root canal treatment. These values can also be shown on the tooth model by means of a colour coding. In case the safety value for the minimal wall thickness is specified, then the parts of the roots with a smaller thickness can also be marked. This latter method gives the user feedback regarding the possible increase of file size in each section without risk for perforation of the root.

Yet another parameter that gives valuable feedback to the user is the curvature of the root canal since this determines the necessary bending of the files during treatment and as such the risk of instrument fracture. The curvature of the root canal can be determined by calculating the curvature of the midline of the root canal in each point of the root canal. This value can be visualized as well by a colour code along the root canal. This value can be compared with the maximal allowable bending of the files that will be used during treatment and as such critical areas (i.e. areas with risk of fracture of the file due to bending exceeding the maximal allowable bending of the endodontic file) can be marked for the user.

According to another step of the current invention, the system allows for simulating the root canal treatment.

An example of root canal treatment simulation is the cleaning of a root canal (i.e. either primary root canal treatment or retreatment). This means that the file sequence as proposed by the system or as specified by the user is applied to the respective root canal and the material removed by the file is removed from the tooth model. As such a 3D model of the post-treatment tooth is created. This post-treatment model can be compared with the pre-treatment model and the removed material can be marked visually either in the 3D model or in the 2D slices. Additionally the volume of the reamed root canal can be calculated in order to quantify the volume that needs to be filled, and as such provide a measure for the necessary quantity of filling material needed during root canal treatment. Another feature of the system is that multiple different treatments can be simulated and the difference between these treatments can be visualized in a similar way as the difference between pre- and post-treatment. This will aid in selecting the optimal cleaning treatment for a specific case.

Another example of root canal treatment simulation is the planning of the endodontic post to provide retention for the prosthetic restoration in cases where there is insufficient remaining tooth structure to retain the core. In a first approach the user can select a post from a library of (glass fiber or metal) posts and place it virtually in the root canal, According to another approach a post is automatically selected from a library of posts based on one (or a combination) of the following criteria: post with dimensions that best fit the dimensions of the reamed root canal, post with dimensions that minimally circumscribes the reamed root canal, post with dimensions that ensures a minimal root wall thickness around the post, post with dimensions that limits the risk of tooth fracture or . . . .

After placing the post it is possible to determine perforations—if any—by determining the intersections between the post and the 3D tooth model. These intersections can be visualized by colour marking either the part of the surface of the post that is outside the tooth model or the intersection lines between post and tooth model. After virtually placing the post it is also possible to visualize the root thickness around the post in order to give the user feedback with respect to either the risk of perforation or the risk of fracture of the tooth root (as a result of the weakening of the tooth due to the post preparation). The same technical methods as described for calculating the root thickness along the root canal can be used for calculating the root thickness around the post. The risk of perforation can be quantified based on threshold values for the root thickness that are clinically accepted. Another way of quantifying the risk of perforation is by taking into account on the one hand the root thickness around the post and on the other hand the clinical deviations in preparing the cavity for the posts (i.e. the deviations between the planned position and orientation of the post and the actual position and orientation). The main cause of these deviations is the limitation of the operator in transferring the planning to the patient, which is also due to the limitations of the instrumentation used. Another method for quantifying the risk of perforations is by using a statistical model obtained by retrospectively analyzing a large number of tooth-root preparations for post placement including those with and without perforations. The risk of fracture can be quantified by including a mechanical strength analysis of the prepared tooth root (e.g. simplified mechanical model or finite element model). Another way of quantifying the risk of fracture is by means of applying a statistical model. Such a statistical model will include besides the root thickness around the post a number of other parameters like bite forces, gender, tooth type or size . . . for predicting the fracture risk.

According to yet another example the planning software also aids in determining the dimensions of the core build-up to replace the missing tooth material in order to strengthen the tooth to prevent breakage. Therefore, either an expert system is set up to propose an ideal core build-up or tools are provided to the user for manually creating a core build-up and allowing to perform an analysis for verifying for example the resulting tooth strength, the chances for a successful crown restoration . . . . For the latter the planning software will also need to allow the user to create the crown restoration, either by importing a wax-up, or by selecting, positioning, and if needed adapting a crown from a library of crowns, or by mirroring the patient's contra-lateral crown, or by using a statistical model for fitting a crown in between the neighbouring teeth, or by any other possible method. Feedback can then be given to the user with respect to the available thickness for the restorative crown in order to estimate the risk of fracture of the crown or possibly crown perforations. As such the post selection and positioning, and the core build-up can be optimized prior to the root canal treatment in order to reduce clinical risks or failure within the patient. According to another preferential implementation, the remaining information of the tooth/tooth root is compared against a parameterized 3D statistical model of the relevant tooth type. The statistical model of the tooth is aligned with and modified according to a best fit with said remaining part of the tooth/tooth root. The missing information required to perform the prosthetic restoration (e.g. information of the crown) is given as the difference between the remaining tooth and the modified statistical model.

The ideal post could also be automatically selected from a library and automatically positioned in the 3D model of the tooth. Therefore an expert system is set up that takes into account all necessary parameters (e.g. root anatomy, restorative crown, strength of tooth with post . . . ) in order to propose a clinically relevant size and position for the post for each individual case. This expert system can either consist of a set of clinically applied rules or be a statistical model generated by a retrospective analysis of successful cases, or any type of heuristic.

Figure 1:
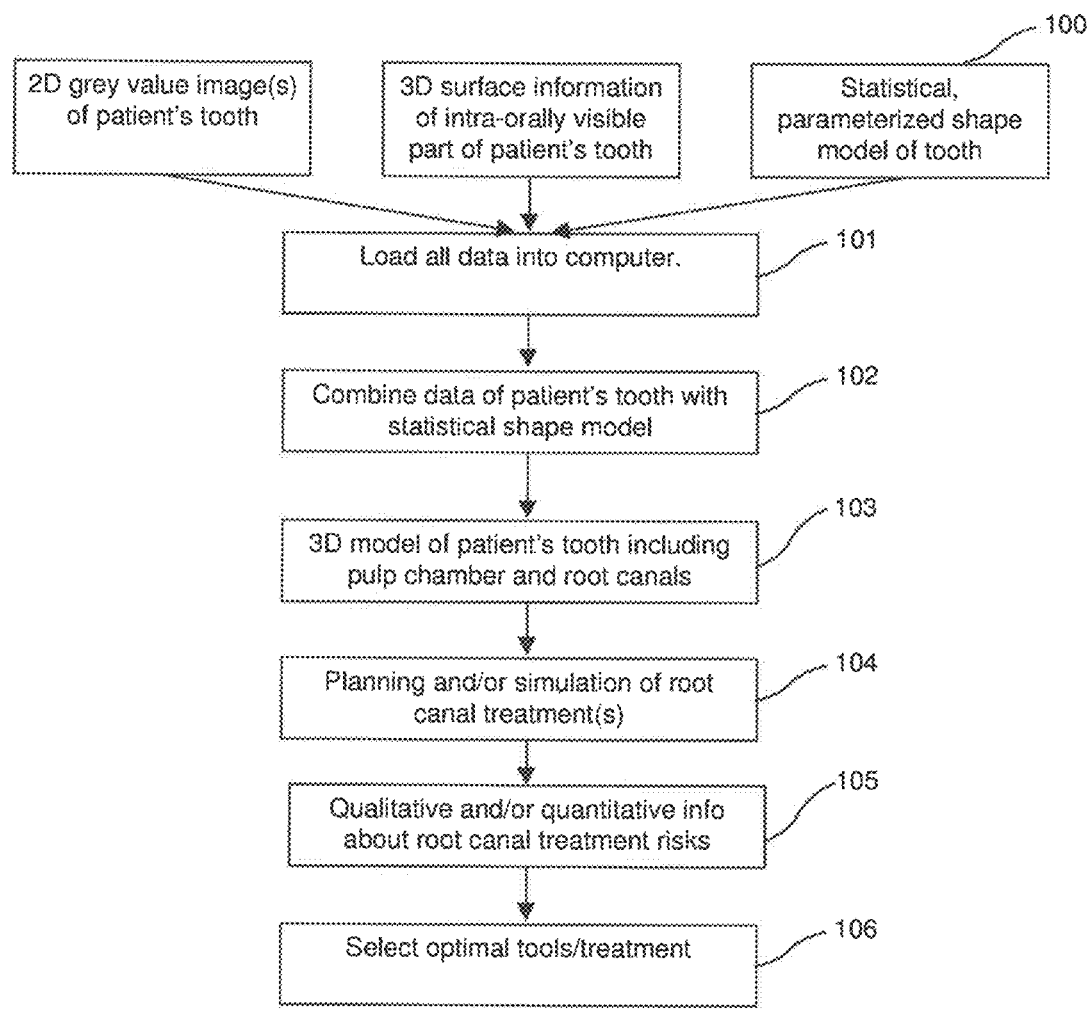
FIG. 1 shows a flowchart visualizing the input and the different steps of the method for 3D root canal treatment planning according to an embodiment of the present invention.
Figure 2:
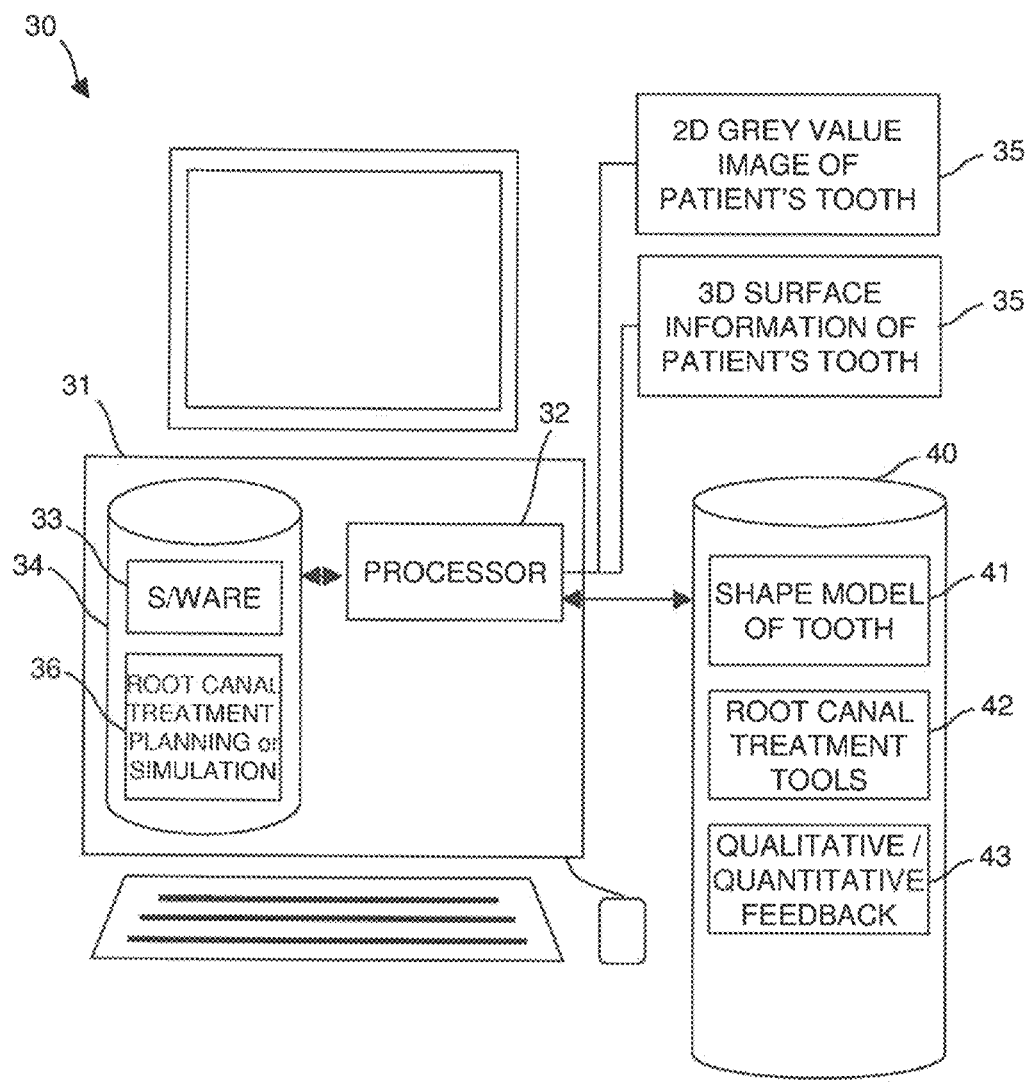
FIG. 2 shows a system and software for 3D root canal treatment planning according to an embodiment of the present invention.

All methods according to embodiments of the present invention and systems according to the present invention can be implemented on computer equipment 30 that is adapted to implement methods of the present invention. A schematic representation of such a computer system 30 is shown in FIG. 2 which includes a computer 31 with a processor 32 and memory and preferably a display. Such methods can be based on the computer 31 having means for generating and visualizing a 3D model, e.g. including the pulp chamber and root canals, of the tooth to be treated, Such a method can be implemented on a computer 31 by providing software that when run on the computer allows the combination of at least one piece of tooth specific digital information, e.g. 2D grey value image of a patient's tooth 35, and/or a 3D surface information of a patient's tooth 36 with a statistical, parameterized shape model of each tooth type obtained by module 41. The tooth type can be upper or lower incisors, canines, pre-molars, or molars. For achieving this, an input device is provided for inputting data for the 3D model, e.g. from a storage device such as a CD-ROM, or solid state memory or via a network link, e.g. via a LAN or WAN.

The method can be implemented on a computer 31 by providing software 33, e.g. as module 36 that when run on a computer allows planning and/or simulating the root canal treatment on the generated 3D model of the tooth. The software is adapted such that when run on a computer it has a module 43 which allows providing qualitative and/or quantitative feedback relative about the effect of the planned/simulated treatment on the 3D model. It also allows selecting or determining of an approach, e.g. the best approach to the root canal treatment. The computer system can comprise an expert system set up to propose an ideal treatment such as a core build-up or tools 42 are provided to the user for manually creating a core build-up and allowing to perform an analysis for verifying the treatment.

The computer 31 can comprise a processor 32 and a memory 34, 40 which stores machine-readable instructions (software as described above) which, when executed by the processor cause the processor to perform the described methods—A computing system which can be utilized with the methods of the present invention may run computer programs such as 3-Matic™ as supplied by Materialise N.V., Leuven, Belgium. The computer may include a video display terminal, a data input means such as a keyboard, and a graphic user interface indicating means such as a mouse. The computer may be implemented as a general purpose computer, e.g. a UNIX workstation or a personal computer.

The computer 31 typically includes a Central Processing Unit ("CPU"), such as a conventional microprocessor of which a Pentium processor supplied by Intel Corp. USA is only an example, and a number of other units interconnected via bus system. The bus system may be any suitable bus system. The computer includes at least one memory. Memory may include any of a variety of data storage devices known to the skilled person such as random-access memory ("RAM"), read-only memory ("ROM"), and non-volatile read/write memory such as a hard disc as known to the skilled person. For example, the computer may further include random-access memory ("RAM"), read-only memory ("ROM"), as well as a display adapter for connecting the system bus to a video display terminal, and an optional input/output (I/O) adapter for connecting peripheral devices (e.g., disk and tape drives) to the system bus. The video display terminal can be the visual output of computer, and can be any suitable display device such as a CRT-based video display well-known in the art of computer hardware. However, with a desk-top computer, a portable or a notebook-based computer, the video display terminal can be replaced with a LCD-based or a gas plasma-based flat panel display. The computer further includes an user interface adapter for connecting a keyboard, mouse, and optional speaker.

The computer can also include a graphical user interface that resides within machine-readable media to direct the operation of the computer. Any suitable machine-readable media may retain the graphical user interface, such as a random access memory (RAM), a read-only memory (ROM), a magnetic diskette, magnetic tape, or optical disk (the last three being located in disk and tape drives). Any suitable operating system and associated graphical user interface (e.g., Microsoft Windows, Linux) may direct CPU. In addition, computer includes a control program that resides within computer memory storage. Control program contains instructions that when executed on CPU allow the computer to carry out the operations described with respect to any of the methods of the present invention.

The graphical user interface is used to visualize the 3D model, including the pulp chamber and root canals, of the tooth to be treated. It can also be used for planning and/or simulating the root canal treatment on the generated 3D model of the tooth. It can also be used for visualising qualitative and/or quantitative feedback relative about the effect of the planned/simulated treatment on the 3D model and it can also be used for visualizing the selecting or determining of an approach or the best approach to the root canal treatment.

Those skilled in the art will appreciate that other peripheral devices such as optical disk media, audio adapters, or chip programming devices, such as PAL or EPROM programming devices well-known in the art of computer hardware, and the like may be utilized in addition to or in place of the hardware already described.

The computer program product for carrying out the method of the present invention can reside in any suitable memory and the present invention applies equally regardless of the particular type of signal bearing media used to actually store the computer program product. Examples of computer readable signal bearing media include: recordable type media such as floppy disks and CD ROMs, solid state memories, tape storage devices, magnetic disks.

Accordingly, the present invention also includes a software product which when executed on a suitable computing device carries out any of the methods of the present invention. Suitable software can be obtained by programming in a suitable high level language such as C and compiling on a suitable compiler for the target computer processor, Such methods will now be described.

According to step 100 of the method, a 2D grey value image is taken of the patient's tooth; 3D surface information of the intra-orally visible part of the patient's tooth is digitized; and a statistical, parameterized shape model of the respective tooth (e.g. incisor, canine, premolar, or molar) is made available.

At step 101 all data is loaded into a computer—such as computer 31 above, Computer 31 is adapted to carry out any of the methods of the present invention.

At step 102 the 2D and 3D information of the patient's tooth is combined with the statistical, parameterized shape model by means of a dedicated software application, i.e. as run on computer 31. This software application can operate either fully automatically or semi-automatically (i.e. requiring user input at well defined steps of the algorithm), The use of a statistical, parameterized shape model (also known as an active shape model) in combination with 2D grey value images or 3D surface information is known and described in literature for various applications (*Nonrigid 3-D/2-D registration of images using statistical models. In: MICCAI. Volumes LNCS* 1679, 138-147, 1999; *Biogeneric tooth: a new mathematical representation for tooth morphology in lower first molars. Eur Oral Sci* 113, 333-340, 2005; *Registration algorithm for statistical bone shape reconstruction from radiographs—an accuracy study, Proceedings of the 29$^{th}$ Annual International Conference of the IEEE Engineering in Medicine and Biology Society,* 6375-6378, 2007; *Evaluation and enhancement of a procedure for generating 3D bone model using radiographs, Advances in Medical Engineering, Proceedings in Physics* 114, 163-168, 2007; *2D/3D deformable registration using a hybrid atlas. In: MICCAI. Volume LNCS* 3750, 223-230, 2005). A parameterized statistical shape model of a tooth including the internal geometry (i.e. pulp chamber and root canals) can be obtained as follows.

A large set of natural human teeth of a certain tooth type (incisors, canines, premolars, or molars) is digitized in order to obtain a three-dimensional description of both the outer shape (crown and root) and the internal shape (pulp chamber and root canals). Digitizing these teeth can be done for example by taken μCT scans of the teeth, which are then processed by a software program such as SimPlant™ supplied by Materialise Dental, Leuven, Belgium in order to generate digital three-dimensional descriptions of the internal and external shape of these teeth. The three-dimensional description of the tooth can be a surface model, a set of anatomical landmarks/points characterizing the tooth shape, a volumetric model or yet any other 3D representation detailing the internal and external shape of the tooth. The selected set of natural human teeth must be a representative sample of the population for which the parameterized statistical shape model will be used. Thus, this set of natural human teeth must reflect the natural variations in external and internal three-dimensional shape of that type of human tooth within the population of interest.

First a coordinate reference is established for the digitized set of natural teeth in order to align all teeth, which means that position, scale and rotational effects are filtered out. Now the variation in shapes within this coordinate reference for the set of natural teeth can be analysed and described. One example for describing the variation in shapes is by means of principal components. Therefore a principal component analysis is performed on the set of aligned natural human teeth, which is in fact a statistical analysis resulting in eigenvectors and eigenvalues. These eigenvectors (or principal components) are uncorrelated variables/parameters describing the variation in shapes. The eigenvectors are ordered by their eigenvalue, highest to lowest, to give the components in order of significance. The eigenvector with the highest eigenvalue describes the largest variation in shape. The parameterized statistical model/description of the three-dimensional shape of the tooth (including internal pulp chamber and root canals) is in fact the linear combination of either all these eigenvectors or a set of these eigenvectors (i.e. leaving out the eigenvectors of lesser significance, thus with low eigenvalues), Varying the parameter values (i.e. the values with which the eigenvectors are multiplied) in the statistical model changes its three-dimensional shape and allows for it to be brought into exact correspondence (in terms of shape and geometry) with the 3D description of any tooth used in the initial analysis used to create the statistical model in case the statistical shape model is based on all eigenvectors. When only using a subset of the eigenvectors the correspondence will not be exact but a good approximation will be obtained since only eigenvectors of lesser significance are not added to the statistical shape model. In addition, the parameters can be used to bring the statistical model into approximate correspondence to any tooth of the same type but foreign to the original set of teeth used to create the statistical model. The better the set of natural human teeth used to create the parameterized statistical model reflects all shape variations in human teeth, the more accurate the statistical shape model can be brought into correspondence to any new example of such a tooth.

In an approach according to an embodiment of the present invention the parameterized statistical model is used in combination with 3D crown surface information (i.e. intra-orally visible part) and one or more 2D grey value images of a patient's tooth. The aim is to create a three-dimensional representation of this patient's tooth by means of combining the patient specific information with the parameterized, statistical shape model in such a manner that the result approximates as well as possible the real anatomy of the tooth as present in the patient's mouth. Therefore, at first the patient specific tooth information (3D crown surface and 2D grey value images) is aligned with the parameterized statistical shape model, which means that all available data is positioned within a same coordinate system. Then the parameter values of the statistical shape model are iteratively changed in order to modify its shape and geometry in order to match with on the one hand the 3D crown information and with on the other hand the 2D grey value image(s) and this according to a predefined criterion. The criterion for the fitting on the 3D crown information can be minimizing the distance between the statistical shape model at crown level and the 3D crown information. The criterion for the fitting on the 2D grey value image(s) can be minimizing the distance between the projection outlines of the internal and external shape of the tooth of the statistical shape model in planes estimated to correspond to the projection plane(s) of the 2D grey value image(s). These criterions must be combined in order to obtain the best fitting 3D description of the patient's tooth that reflects the internal and external shape with sufficient detail and accuracy.

Another approach according to an embodiment of the present invention for obtaining a parameterized statistical shape model of a tooth including the internal geometry (i.e. pulp chamber and root canals) is the following. In addition to digitizing the set of natural human teeth in order to obtain a 3D description (same as mentioned above) 2D grey value image(s) can be taken of these teeth and digitized. The combined 2d and 3D data of each tooth within the set can be analyzed statistically in order to obtain a parameterized shape model including a 3D shape model and an associated parameterized 2D grey value image(s), in which certain components/parameters of the shape model are directly linked to parameters of the 2D grey value image(s). As such the covariances between the statistical shape model and its corresponding parameterized 2D grey value image(s) are known. Fitting this parameterized statistical shape model onto the 2D grey value images of the patient's tooth can be done by iteratively modifying parameters of the parameterized 2D grey value image(s), which will result in a corresponding modification of the 3D shape model, until a good match is obtained. This can further be combined with matching the parameterized statistical shape model onto the 3D crown information of the patient's tooth. As such a 3D model of the patient's tooth is obtained that includes external geometry, shape and location of the pulp chamber and root canals.

The result is a detailed 3D model of the patient's tooth including a 3D representation of the pulp chamber and root canals, which is visualized at step 103. Different visualization modes, such as for example 3D surface renderings, sectional images, transparency mode, volume renderings . . . can be made available through the software application in order to allow the dentist or dental specialist to fully assess the three-dimensional complexity of the root canals and pulp chamber.

At step 104 planning and/or simulation of root canal treatment is done by means of the software application. This step may include the use of software tools in combination with a digital library of root canal treatment tools (e.g. endodontic files, endodontic posts . . . ).

At step 105 qualitative and/or quantitative information is provided to the dentist or dental specialist about the root canal treatment risk. Different visualization modes, such as for example equidistant lines, colour bands, histograms . . . , can be included in the software application to clearly present the qualitative and/or quantitative feedback to the dentist or dental specialist. This allows the dentist or dental specialist to analyse risks related to the simulated root canal treatment.

At step 106 optimal tools or root canal treatment is selected.

The invention claimed is:
1. A method for 3D planning of the restoration of a tooth comprising the steps of:
   generating and visualizing a 3D model of the tooth to be restored by combining at least one piece of tooth specific digital information with a statistical, param- eterized shape model of the relevant tooth type, wherein the 3D model includes the root canals and pulp chamber;

planning or simulating a root canal treatment on the generated 3D model of the tooth creating a post-treatment 3D model of the tooth;

allowing determining the dimensions of a core build-up to replace missing tooth material in the post-treatment 3D model in order to strengthen the tooth to prevent breakage;

creating a crown restoration on the post-treatment 3D tooth model by importing a wax-up or by selecting, positioning, and adapting a crown from a library of crowns in the post-treatment 3D model of the tooth, or by mirroring the existing contra-lateral crown of the patient, or by using a statistical model for fitting a crown in between the neighboring teeth of the tooth to be restored;

creating a visualization on the post-treatment 3D model of the tooth of a quantitative feedback of the available thickness of the remaining material of the tooth for the restorative crown and estimate the risk of fracture of the crown or possible crown perforations; and selecting or determining an optimal core build-up and sequence of treatment steps for the crown restoration for ensuring tooth strength and successful crown restoration.

2. The method of claim 1, wherein the step of allowing determining the dimensions of a core build-up to replace missing tooth material in the post-treatment 3D model in order to strengthen the tooth to prevent breakage comprises providing automatically an ideal core-build up.

3. The method of claim 1, wherein the step of allowing determining the dimensions of a core build-up to replace missing tooth material in the post-treatment 3D model in order to strengthen the tooth to prevent breakage comprises providing tools for the user for manually creating a core build up.

4. The method of claim 1, comprising the further steps of:
allowing selecting of a post to provide retention for the crown restoration from a library of posts and positioning it in the reamed root canal of the post-treatment 3D model of the tooth;
creating a visualization on the post-treatment 3D model of the tooth of a quantitative feedback on the risk of perforation or the risk of fracture of the tooth root as a result of the post positioning; and
selecting or determining the optimal post and post position in order to reduce clinical risks or failure of the crown restoration, wherein this step develops a sequence of treatment steps for the preparation of the cavity and root canal for the post.

5. The method of claim 4, wherein the post is automatically selected from a library of posts based on one or a combination of the following criteria: post with dimensions that best fit the dimensions of the reamed root canal of the post-treatment 3D tooth model, post with dimensions that minimally circumscribes the reamed root canal of the post-treatment 3D tooth model, post with dimensions that ensures a minimal root wall thickness around the post, post with dimensions that limits the risk of tooth fracture.

6. The method of claim 4, wherein the post is manually selected from a library of posts.

7. The method of claim 4, wherein the post is automatically positioned in the post-treatment 3D model of the tooth.

8. The method of claim 4, wherein the post is manually positioned in the post-treatment 3D model of the tooth.

9. The method of claim 4, wherein the visualization on the post-treatment 3D model of the tooth of a quantitative feedback on the risk of perforation or the risk of fracture of the tooth root as a result of the post positioning comprises a visualization of the intersections between the post and the post-treatment 3D tooth model by color marking either the part of the surface of the post that is outside the post-treatment 3D tooth model or the intersection lines between the post and the post-treatment 3D tooth model.

10. The method of claim 5, wherein the visualization on the post-treatment 3D model of the tooth of a quantitative feedback on the risk of perforation or the risk of fracture of the tooth root as a result of the post positioning comprises a visualization of the root thickness around the post; and wherein the risk of perforation is quantified based on clinically accepted threshold values for the root thickness around the post.

11. The method of claim 4, wherein the risk of perforation is quantified by using a statistical model.

12. The method of claim 1, wherein the 3D model is obtained from 2D grey value image(s) of patient's tooth and 3D surface information of an intra-orally visible part of patient's tooth.

13. The method according to claim 12 wherein the 2D grey value image(s), 3D surface information and statistical, parametrized shape model of each tooth type are loaded in a computer.

14. The method of claim 5, wherein the risk of perforation is quantified by using a statistical model.

15. The method of claim 6, wherein the risk of perforation is quantified by using a statistical model.

16. The method of claim 7, wherein the risk of perforation is quantified by using a statistical model.

17. The method of claim 2, wherein the 3D model is obtained from 2D grey value image(s) of patient's tooth and 3D surface information of an intra-orally visible part of patient's tooth.

18. The method of claim 2, further comprising the steps of:
allowing selecting of a post to provide retention for the crown restoration from a library of posts and positioning it in the reamed root canal of the post-treatment 3D model of the tooth;
creating a visualization on the post-treatment 3D model of the tooth of a quantitative feedback on the risk of perforation or the risk of fracture of the tooth root as a result of the post positioning; and
selecting or determining the optimal post and post position in order to reduce clinical risks or failure of the crown restoration, wherein this step develops a sequence of treatment steps for the preparation of the cavity and root canal for the post.

19. The method of claim 3, further comprising the steps of:
allowing selecting of a post to provide retention for the crown restoration from a library of posts and positioning it in the reamed root canal of the post-treatment 3D model of the tooth;
creating a visualization on the post-treatment 3D model of the tooth of a quantitative feedback on the risk of perforation or the risk of fracture of the tooth root as a result of the post positioning; and
selecting or determining the optimal post and post position in order to reduce clinical risks or failure of the crown restoration, wherein this step develops a sequence of treatment steps for the preparation of the cavity and root canal for the post.

20. A non-transitory storage medium storing a computer program product which when executed on a computer causes the computer to perform a method for 3D planning of the restoration of a tooth comprising the steps of:

generating and visualizing a 3D model of the tooth to be restored by combining at least one piece of tooth specific digital information with a statistical, parameterized shape model of the relevant tooth type, wherein the 3D model includes the root canals and pulp chamber;

planning or simulating a root canal treatment on the generated 3D model of the tooth creating a post-treatment 3D model of the tooth;

allowing determining the dimensions of a core build-up to replace missing tooth material in the post-treatment 3D model in order to strengthen the tooth to prevent breakage;

creating a crown restoration on the post-treatment 3D tooth model by importing a wax-up or by selecting, positioning, and adapting a crown from a library of crowns in the post-treatment 3D model of the tooth, or by mirroring the existing contra-lateral crown of the patient, or by using a statistical model for fitting a crown in between the neighboring teeth of the tooth to be restored;

creating a visualization on the post-treatment 3D model of the tooth of a quantitative feedback of the available thickness of the remaining material of the tooth for the restorative crown and estimate the risk of fracture of the crown or possible crown perforations; and selecting or determining an optimal core build-up and sequence of treatment steps for the crown restoration for ensuring tooth strength and successful crown restoration.

\* \* \* \* \*